United States Patent [19]

Woodward et al.

[11] Patent Number: 5,352,708
[45] Date of Patent: Oct. 4, 1994

[54] NON-ACIDIC CYCLOPENTANE HEPTANOIC ACID, 2-CYCLOALKYL OR ARYLALKYL DERIVATIVES AS THERAPEUTIC AGENTS

[75] Inventors: David F. Woodward, El Toro; Steven W. Andrews; Robert M. Burk, both of Irvine; Michael E. Garst, Newport Beach, all of Calif.

[73] Assignee: Allergan, Inc., Irvine, Calif.

[21] Appl. No.: 948,056

[22] Filed: Sep. 21, 1992

[51] Int. Cl.$^5$ .......................................... A61K 31/045
[52] U.S. Cl. ................................................... 514/729
[58] Field of Search .................. 514/729; 568/330, 807

[56] References Cited

U.S. PATENT DOCUMENTS

| | | | |
|---|---|---|---|
| 4,055,602 | 10/1977 | Nelson | 568/807 |
| 4,171,331 | 10/1979 | Biddlecom et al. | 568/807 |
| 4,183,870 | 1/1980 | Caton | 568/330 |
| 4,599,353 | 7/1986 | Bito . | |
| 4,994,274 | 2/1991 | Chan et al. . | |
| 5,034,413 | 7/1991 | Chan et al. . | |

FOREIGN PATENT DOCUMENTS

| | | |
|---|---|---|
| 0093380 | 11/1983 | European Pat. Off. . |
| 0102230 | 7/1984 | European Pat. Off. . |
| 0253094 | 1/1988 | European Pat. Off. . |
| 0364417 | 6/1989 | European Pat. Off. . |
| 0453127 | 10/1991 | European Pat. Off. . |
| 2721534 | 12/1977 | Fed. Rep. of Germany . |
| 2312240 | 12/1976 | France . |
| 2386523 | 11/1978 | France . |
| 2402644 | 3/1979 | France . |
| 68940 | 2/1974 | Luxembourg . |
| 90/02553 | 3/1990 | PCT Int'l Appl. . |
| 92/08465 | 5/1992 | PCT Int'l Appl. . |

OTHER PUBLICATIONS

Prostaglandins: vol. 13, No. 5, May 1977, Stoneham, Mass., pp. 837–843, H. C. Arndt, "The Synthesis and Biological Activity of Prostaglandins Analogs Containing Spiroocyclic Rings".
Tetrahedron: vol. 32, 1976, Oxford GB, pp. 2747–2752, P. DeClercq et al, "Cyclopentanones–XV1,. Prostaglandin Synthesis Involving Catalytic Hydrogenation of 2,3-Dialkyl-4-Hydroxy-2-Cyclopentenones".
Derwent Publications Ltd., London, GB; AN 71-57222S & JP,A,46 030 830 (Ono Pharmaceutical Co).
Bito, Laszlo Z., "Prostaglandins, Old Concepts and New Perspectives," *Arch Ophth.* vol. 105, Aug. 1987 pp. 1036–1039.
Siebold, et al., "Esterified prostaglandin shows 'potent' promise", *Prodrug* 5,3, Feb. 1, 1989.
Starr, Michael S., "Further Studies on the Effect of Prostaglandin on Intraocular Pressure in the Rabbit," *Exp. Eye Res.*, (1971) 170–177.
Nilsson, Siv F. E., et al., "PGF2a Increases Uveoscleral Outflow," ARVO Abstracts, p. 284 Invest. Ophthalmol. Vis.Sci. 28 (suppl) (1987).
Bito, Laszlo Z., "Prostaglandins, Other Eicosanoids, and Their Derivatives as Potential Antiglaucoma Agents," Applied Pharmacology in the Medical Treatment of Glaucomas Drance, S. M. and Neufeld, A. H. eds, New York, Grune & Stratton, 1984 pp. 477–505.
Bito, Laszlo Z., "Prostaglandins and Related Compounds as Potential Ocular Therapeutic Agents," Biological Protection with Prosataglandins (Cohen, M. M., ed., Boca Raton, Fla., CRC Press Inc., 1985, pp. 231–252.

*Primary Examiner*—Robert Gerstl
*Attorney, Agent, or Firm*—Robert J. Baran; Martin A. Voet; Howard R. Lambert

[57] ABSTRACT

The present invention provides cyclopentane heptanoic acid, 2-cycloalkyl or arylalkyl derivatives, substituted in the 1-position with halo, methyl, hydroxyl, nitro, amino, amido, azido, oxime, cyano, thiol, either or thioether groups, e.g., a 1-OH cyclopentane heptanoic acid, 2-(cycloalkyl or arylalkyl) derivatives. The cyclopentane heptanoic acid, 2-(cycloalkyl or arylalkyl) derivatives of the present invention are potent ocular hypotensives, and are particularly suitable for the management of glaucoma. Moreover, the cyclopentane heptanoic, 2-(cycloalkyl or arylalkyl) derivatives of this invention are smooth muscle relaxants with broad application in systemic hypertensive and pulmonary diseases; smooth muscle relaxants with application in gastrointestinal disease, reproduction, fertility, incontinence, shock, etc.

8 Claims, 3 Drawing Sheets

Fig. 2.

Fig. 3.

NON-ACIDIC CYCLOPENTANE HEPTANOIC ACID, 2-CYCLOALKYL OR ARYLALKYL DERIVATIVES AS THERAPEUTIC AGENTS

FIELD OF THE INVENTION

The present invention relates to cyclopentane heptanoic acid, 2-cycloalkyl or arylalkyl derivatives, substituted in the 1-position with halo, hydryl, hydroxyl, nitro, amino, amido, azido, oxime, cyano, thiol, ether or thioether groups, e.g., 1-OH cyclopentane heptanoic acid, 2-(cycloalkyl or arylalkyl) derivatives. The cyclopentane heptanoic acid, 2-(cycloalkyl or arylalkyl) derivatives of the present invention are potent ocular hypotensives, and are particularly suitable for the management of glaucoma. Moreover, the cyclopentane heptanoic acid, 2-(cycloalkyl or arylalkyl) derivatives of this invention are smooth muscle relaxants with broad application in systemic hypertensive and pulmonary diseases; smooth muscle relaxants with application in gastrointestinal disease, reproduction, fertility, incontinence, shock, etc.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical $\beta$-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S., *Exp. Eye Res.*, 1971, 11, P.P. 170–177; Bito, L. Z. *Biological Protection with Prostaglandins* Cohen, M. M., ed., Boca Raton, Fla., CRC Press Inc., 1985, pp 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_5$ alkyl esters. e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch, Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending U.S. patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl; 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11, 15- 9,15- and 9,11-diesters of prostaglandins, for example 11,15-dipivaloyl $PGF_{2\alpha}$ are known to have ocular hypotensive activity. See the copending U.S. patent applications Ser. No. 385,645 filed 27 Jul. 1990, now U.S. Pat. No. 4,494,274; 584,370 which is a continuation of U.S. Ser. No. 386,312, and 585,284, now U.S. Pat. No. 5,034,413 which is a continuation of U.S. Ser. No. 386,834, where the parent applications were filed on 27 Jul. 1989. The disclosures of these patent applications are hereby expressly incorporated by reference.

SUMMARY OF THE INVENTION

We have found that certain cyclopentane heptanoic acid, 2-cycloalkyl or arylalkyl derivatives wherein the carboxylic acid group is replaced by a non-acidic substituent have pronounced effects on smooth muscle and are potent ocular hypotensive agents. We have further found that such compounds may be significantly more potent than their respective parent compounds and, in the case of glaucoma surprisingly, cause no or significantly lower ocular surface hyperemia than the parent compounds.

The present invention relates to methods of treating cardiovascular, pulmonary-respiratory, gastrointestinal, reproductive and allergic diseases, shock and ocular hypertension which comprises administering an effective amount of a nonacidic derivative of cyclopentane heptanoic acid, 2-cycloalkyl or arylalkyl represented by the formula I wherein A is an alkylene or alkenylene radical having from two to six carbon atoms, e.g. about four to five carbon atoms, which radical may be substituted with one or more hydroxy, oxo, alkyloxy or alkylcarboxy groups, and B is a cycloalkyl radical having from three to seven carbon atoms, e.g. about five to six carbon atoms, or an aryl radical, selected from the group consisting of hydrocarbyl aryl and heteroaryl radicals wherein the heteroatom is selected from the group consisting of nitrogen, oxygen and sulfur atoms, and $R_1$, $R_2$ and X are as defined below. For example, A may be a straight chain alkylene radical, e.g. pentylene, or alkenylene radical, e.g. 3-hydroxy-1-pentylenyl, and B may be selected from the group consisting of cyclopentyl, cyclohexyl, phenyl, thienyl, furanyl, pyridyl, etc. B may also be substituted by radicals represented by Y, as defined below.

More preferably the method of the present invention comprises administering a non-acidic derivative of cyclopentane heptanoic acid, 2-(phenyl alkyl) represented by the formula II wherein y is 0 or 1 and either the α or ω chain may be unsaturated, Y is a radical selected from the group consisting of halo, e.g. fluoro, chloro, etc., nitro, amino, thiol, hydroxy, alkyloxy, alkylcarboxy, etc. and n is 0 or an integer of from 1 to about 3 and the symbols $R_1$, $R_2$, $R_3$ and X are as defined below. Preferably the nonacidic derivative used in the above method of treatment is a compound of formula (III).

wherein hatched lines indicate α configuration, solid triangles are used to indicate β configuration; the dashed bonds represent a single bond or a double bond which can be in the cis or trans configuration; X is a radical selected from the group consisting of halo, hydryl, hydroxyl, nitro, amino, amido, azido, oxime, cyano, thiol, alkoxy (ether) and thio ether radicals; one of $R_1$ and $R_2$ is =O, —OH or a —O(CO)$R_6$ group, and the other one is —OH or —O(CO)$R_6$, or $R_1$ is =O and $R_2$ is H; $R_3$ is =O, OH or O(CO) $R_6$; wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring from about 3 to about 7 carbon atoms, or an aryl or heteroaryl ring, as defined above; or a pharmaceutically acceptable salt thereof. Preferably $R_1$, $R_2$ and $R_3$ are —OH.

In another aspect, the present invention relates to a method of treating cardiovascular, pulmonary-respiratory, gastrointestinal, reproductive and allergic diseases, shock and ocular hypertension which comprises administering to a subject a pharmaceutical composition comprising a therapeutically effective amount of a compound of formula (IV)

wherein the symbols and substituents are as defined above, in combination with a pharmaceutical carrier.

In a further aspect, the present invention relates to pharmaceutical compositions comprising a therapeutically effective amount of a compound of formulae (I), (II), (III), or (IV) wherein the symbols have the above meanings, or a pharmaceutically acceptable salt thereof in admixture with a non-toxic, pharmaceutically acceptable liquid vehicle.

In a still further aspect, the present invention relates to nonacidic cyclopentane heptanoic acid, 5-cis-2-(3-hydroxy-5-phenyl-1-trans-pentyl) derivatives of the above formulae, wherein the substituents and symbols are as defined hereinabove, or a pharmaceutically acceptable salt of such compounds.

DETAILED DESCRIPTION OF THE INVENTION

The present invention relates to the use of cyclopentane heptanoic acid, 2-cycloalkyl or arylalkyl derivatives as therapeutic agents, e.g. as ocular hypotensives. These therapeutic agents are represented by compounds having the formula I, as defined above. The preferred nonacidic cyclopentane heptanoic acid, 2-(phenyl alkyl) derivatives used in accordance with the present invention are encompassed by the following structural formula (II)

wherein the substituents and symbols are as hereinabove defined. More preferably the nonacidic derivatives are represented by formula (III).

wherein the substituents and symbols are as defined above. More preferably, the nonacidic derivatives utilized in the present invention are compounds represented by the formula (IV)

wherein the substituents and the symbols are as defined above.

Most preferably the present invention utilizes the novel nonacidic derivatives of the formula (V)

and their 9- and/or 11- and/or 15-esters.

In all of the above formulae, as well as in those provided hereinafter, the dotted lines on bonds between carbons 5 and 6 (C-5), between carbons 13 and 14 (C-13), between carbons 8 and 12 (C-8), and between carbons 10 and 11 (C-10) indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

In the compounds used in accordance with the present invention, compounds having the C-9 or C-11 or C-15 substituents in the α or β configuration are contemplated. As hereinabove mentioned, in all formulas provided herein broken line attachments to the cyclopentane ring indicate substituents in the α configuration. Thickened solid line attachments to the cyclopentane ring indicate substituents in the β configuration. Also, the broken line attachment of the hydroxyl group or other substituent to the C-11 and C-15 carbon atoms signifies the α configuration.

For the purpose of this invention, unless further limited, the term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of $R_6$ may include a cyclic component, —$(CH_2)_m R_7$, wherein n is 0–10, $R_7$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_7$ preferably is phenyl, and the heteroaromatic rings have oxygen, nitrogen or sulfur as a heteroatom, i.e., $R_7$ may be thienyl, furanyl, pyridyl, etc. Preferably m is 0–4.

X may be selected from the group consisting of: —H, —F, —I, —$NO_2$, —OH,

—$N(R_4)(R_4)$, =N—OH, —C≡N, —SH, —$SR_5$ and —$OR_5$ wherein $R_4$ is hydrogen or $C_1$ to $C_3$ alkyl, and $R_5$ is $C_1$ to $C_3$ alkyl. Preferably $R_4$ is hydrogen.

Preferred representatives of the compounds within the scope of the present invention are the compounds of formula V wherein X is —OH, i.e. cyclopentane heptenol, 5-cis-2-(3-αhydroxy-5-phenyl-1-trans-pentenyl)-3, 5-dihydroxy, [1α, 2β, 3α, 5α] and the 9- and/or 11- and/or 15-esters of this compound. (The numbered designations in brackets refer to the positions on the cyclopentane ring.)

The following novel compounds may be used in the pharmaceutical compositions and the methods of treatment of the present invention.

(1) cyclopentane heptenol-5-cis-2-(3-αhydroxy-5-phenyl-1-trans-pentenyl)-3, 5 dihydroxy, [1α, 2β, 3α, 5α]

(2) cyclopentane heptenamide -5-cis-2-(3-αhydroxy-5-phenyl-1-trans-pentenyl)-3,5 dihydroxy, [1α, 2β, 3α, 5α]

(3) cyclopentane N,N-dimethylheptenamide-5-cis-2-(3-αhydroxy-5-phenyl-1-trans-pentenyl)-3,5 dihydroxy, [1α, 2β, 3α, 5α]

(4) cyclopentane heptenyl methoxide-5-cis-2-(3-αhydroxy-5-phenyl-1-trans-pentenyl)-3,5 dihydroxy, [1α, 2β, 3α, 5α]

(5) cyclopentane heptenyl fluoride-5-cis-2-(3-αhydroxy-5-phenyl-1-trans-pentenyl)-3,5 dihydroxy, [1α, 2β, 3α, 5α]

(6) cyclopentane heptenyl nitrate-5-cis-2-(3-αhydroxy-5-phenyl-1-trans-pentenyl)-3,5 dihydroxy, [1α, 2β, 3α, 5α]

(7) cyclopentane heptenyliodide-5-cis-2-(3-αhydroxy-5-phenyl-1-trans-pentenyl)-3,5 dihydroxy, [1α, 2β, 3α, 5α]

(8) cyclopentane hepteneamine-5-cis-2-(3-αhydroxy-5-phenyl-1-trans-pentenyl)-3,5 dihydroxy, [1α, 2β, 3α, 5α]

(9) cyclopentane heptenecyanide-5-cis-2-(3-αhydroxy -5-phenyl-1-trans-pentenyl)-3,5 dihydroxy, [1α, 2β, 3α, 5α]

(10) cyclopentane hepteneazide-5-cis-2-(3-αhydroxy-5-phenyl-1-trans-pentenyl)-3,5 dihydroxy, [1α, 2β, 3α, 5α]

(11) cyclopentane heptene-5-cis-2-(3-αhydroxy-5-phenyl-1-trans-pentenyl)-3,5 dihydroxy, [1α, 2β, 3α, 5α] (Note when X is —H, i.e. hydryl, the correct designation is heptene.)

(12) cyclopentane N-isopropyl heptene amide-5-cis-2-(3-αhydroxy-5-phenyl-1-trans-pentenyl)-3, 5 dihydroxy, [1α, 2β, 3α, 5α]

(13) cyclopentane N-ethyl heptene amide-5-cis-2-(3-αhydroxy-5-phenyl-1-trans-pentenyl)-3,5 dihydroxy, [1α, 2β, 3α, 5α]

(14) cyclopentane N-methyl heptene amide-5-cis -2-(3-αhydroxy-5-phenyl-1-trans-pentenyl)-3,5 dihydroxy, [1α, 2β, 3α, 5α]

(15) cyclopentane heptenol-5-cis-2-(3-αhydroxy-4-m-chlorophenoxy-1-trans-butenyl)-3,5 dihydroxy, [1α, 2β, 3α, 5α]

(16) cyclopentane heptenamide-5-cis-2-(3-αhydroxy-4-m-chlorophenoxy-1-trans-butenyl)-3,5 dihydroxy, [1α, 2β, 3α, 5α]

(17) cyclopentane heptenol-5-cis-2-(3-αhydroxy-5-phenylpentyl)3,5 dihydroxy, [1α, 2β, 3α, 5α]

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional pharmaceutically-acceptable excipients, e.g. an ophthalmically-acceptable vehicle, and by preparation of unit dosage forms suitable for pharmaceutical use, e.g. topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 μl.

The invention is further illustrated by the following non-limiting Examples.

EXAMPLE 1

Brief Description of the Drawings and Radioligand Binding Studies

Figure 1:
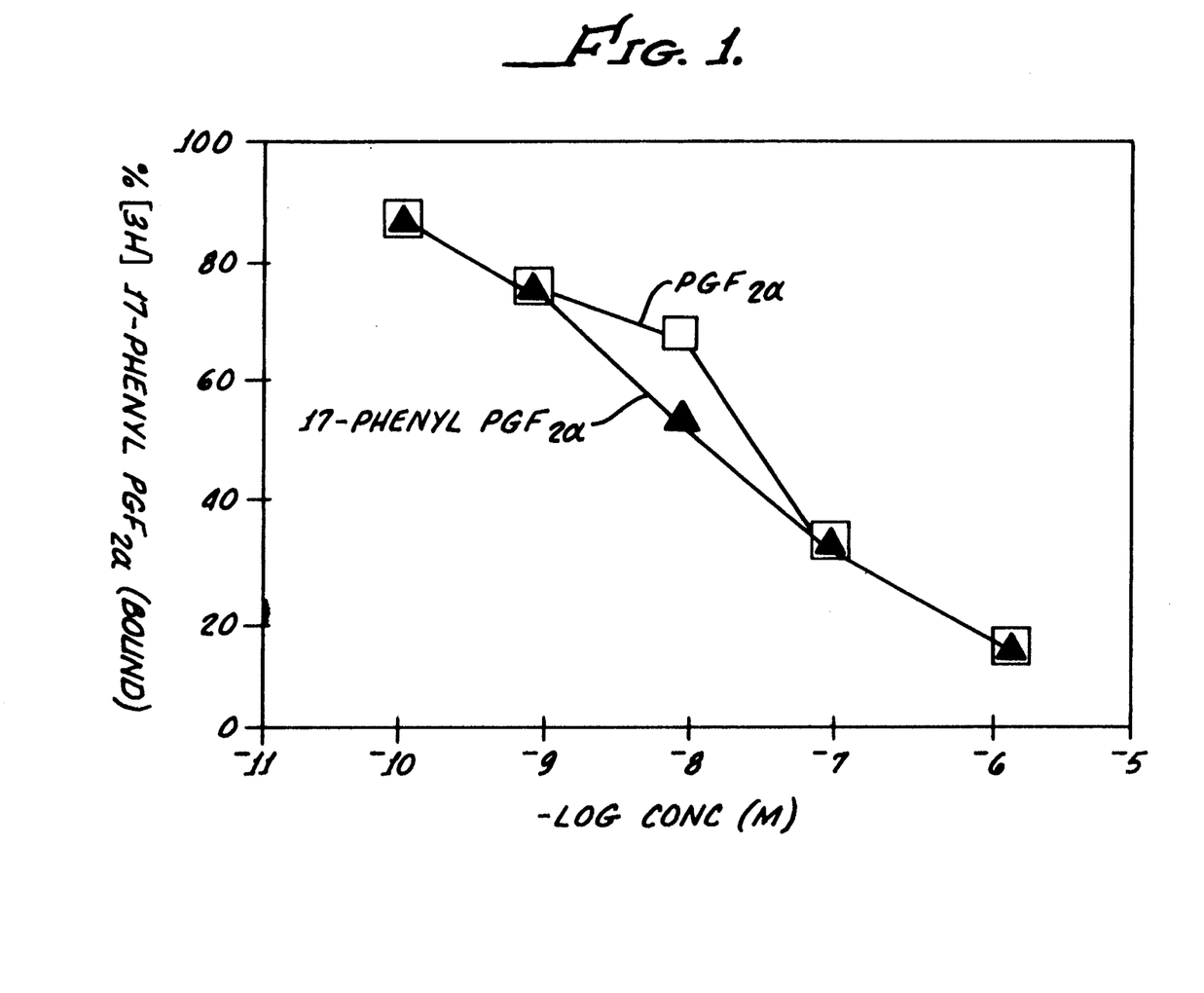
Figure 2:
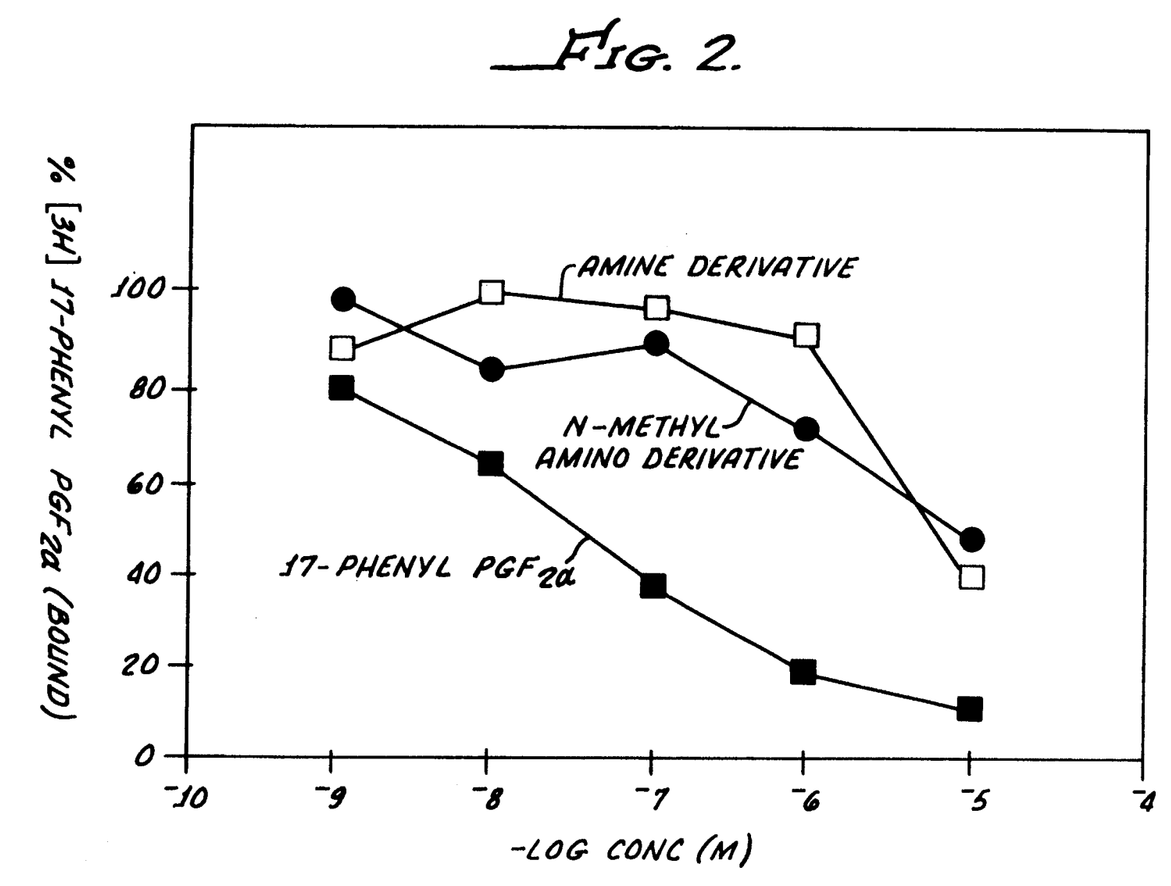
Figure 3:
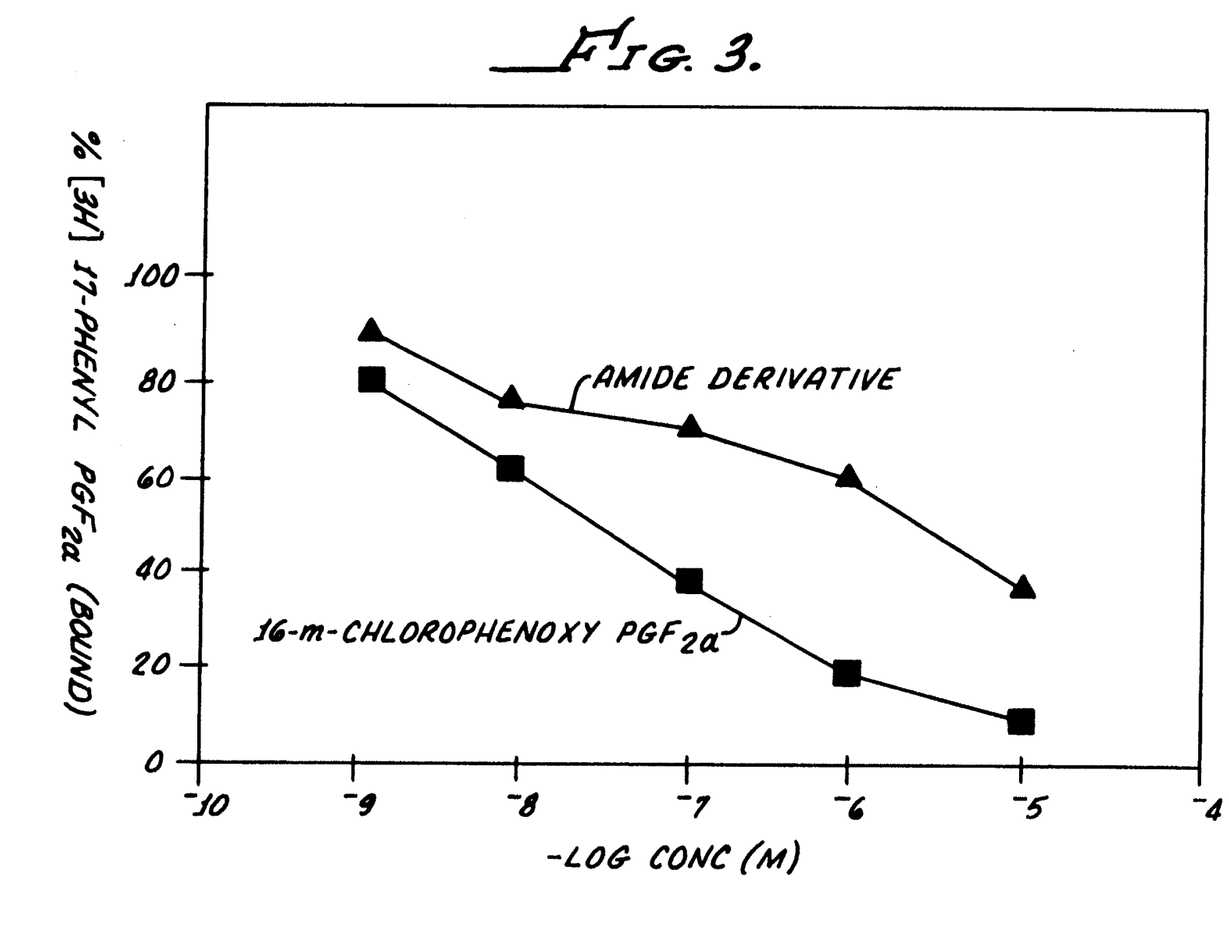

The Radioligand binding studies reported in FIGS. 1 to 3 were performed on plasma membrane preparations from the rat colon. Tissues were homogenized in buffer (0.25M sucrose, 50 mM TRIS: pH 7.4) with a polytron homogenizer for 3 secs at setting 7. The homogenate was centrifuged at 200 g, the supernatant was filtered through gauze, and the filtrate centrifuged at 177,000 g for 40 min. Enriched plasma membrane fractions were subsequently prepared using two-step discontinuous gradients. The 177,000 g pellet was suspended in homogenization buffer and layered over a cushion of 0.842M sucrose for radiolabelled 17-phenyl $PGF_{2\alpha}$ studies. Centrifugation was then performed at 112,700 g for 2 hr. The bands at the interface of the sucrose layers were carefully aspirated and centrifuged at 304,000 g for 40 min. Radioligand binding assays were performed on the pellets, which were suspended with the aid of sonication. Studies with radiolabelled 17-phenyl $PGF_{2\alpha}$ were performed in buffer containing 50 mM TRIS-HCl and 2.5 mM Mn $Cl_2$ at pH 5.75.

Competition studies were performed vs. 5 $nM^3H$-17-phenyl $PGF_{2\alpha}$ in a total volume of 200 μl. Protein concentrations were approximately 40 μg/ml for the colon membrane homogenates. Non-specific binding was determined by 10 μM of the corresponding unlabelled ligand. Studies were terminated by the addition of ice-cold buffer and rapid filtration through Whatman GF/B filters using a Brandel cell harvester.

FIG. 1 shows that prostaglandin $F_{2\alpha}(PGF_{2\alpha})$ and 17-phenyl $PGF_{2\alpha}$ both potently displace $^3H$-17-phenyl $PGF_{2\alpha}$ from its receptor in a dose-related manner. In contrast, $^3H$-17-phenyl $PGF_{2\alpha}$ is not displaced when the terminal —COOH group is replaced by an amine or a methylamide group. See FIG. 2 wherein cyclopentane hepteneamine, 5-cis-2-(3-hydroxy-5-phenyl-1-trans-pentenyl)-3, 5-dihydroxy, [$1_\alpha$, $2_\beta$, $3_\alpha$, $5_\alpha$] and the N-methyl derivative thereof are compared to 17-phenyl $PGF_{2\alpha}$ for their ability to displace $^3H$-17-phenyl $PGF_{2\alpha}$ from its receptor. A further example is provided in FIG. 3 where 16-m-chlorophenoxy $PGF_{2\alpha}$ potently displaces $^3H$-17-phenyl $PGF_{2\alpha}$ but the potent displacement observed for 16-m-chlorophenoxy $PGF_{2\alpha}$ is greatly reduced when the terminal —COOH group is replaced by —$CONH_2$ as in the compound cyclopentane heptenamide, 5-cis-2-(3-hydroxy-4-m-chlorophenoxy-1-trans-butenyl)-3, 5-dihydroxy, [$1_\alpha$, $2_\beta$, $3_\alpha$, $5_\alpha$].

EXAMPLE 2

Ca2+ Signal in Swiss 3T3 Cells

Measurement of intracellular [$Ca^{2+}$] was achieved by incorporating the $Ca^{2+}$-sensitive fluorescent probe Fura-2 AM into Swiss 3T3 cells in suspension as described in Woodward et al. Advances in Prostaglandin, Thromboxane and Leukotriene Research 21:367, 1990. Fluorescence was measured in a Perkin-Elmer LS-5 spectrophotometer at excitation and emission wavelengths of 340 and 492 nM, respectively. Each experimental determination employed $10^6$ cells suspended in Schmuells buffer. For studies in $Ca^{2+}$-free Schmuells buffer, each cuvete also contained 0.4 mM EGTA. Calibration of the Fura 2 signal was as previously described for Quin 2 and Fura 2 Yamagachi et al. J. Biological Chemistry 263: 10745, 1988. Briefly the cells were lysed with digitonin (10 μl×100 mg/ml in DMSO). EGTA (100 mM) and sufficient 10N NaOH to adjust the pH to 8.5 were then successively added to obtain minimum fluorescence.

The effects of the compounds examined on intracellular [$Ca^{2+}$] are compared as the concentration required to produce 50% of the maximal $PGF_{2\alpha}$ response (Table 1). Note that replacement of the terminal —COOH group by a non-acidic substituent universally results in a dramatic reduction in activity.

TABLE 1

| Effect on [$Ca^{2+}$] in Swiss 3T3 Cells | |
|---|---|
| PARENT COMPOUND (1-DERIVATIVE) | E.C.$_{50}$ [nM] |
| $PGF_{2\alpha}$ | 50 |
| A($CONH_2$) | |
| A($CON(CH_3)_2$) | 65000 |
| A(OH) | >10,000 |
| A($OCH_3$) | >10,000 |
| A(F) | >10,000 |
| A($NO_2$) | >10,000 |
| A($NH_2$) | >10,000 |
| A(I) | >10,000 |
| A(CN) | >10,000 |
| A($N_3$) | >10,000 |
| A($CH_3$) | >10,000 |
| 17-phenyl $PGF_{2\alpha}$ | 13 |
| B($CONH_2$) | 900 |
| B(OH) | >10,000 |

A is a cyclopentane heptenoic acid, 5-cis-2-(3-α-hydroxy-1-trans-octenyl)-3, 5-dihydroxy, [$1_\alpha$, $2_\beta$, $3_\alpha$, $5_\alpha$]
B is a cyclopentane heptanoic acid, 5-cis-2-(3-α-hydroxy-5-phenyl-1-trans-pentenyl)-3, 5-dihydroxy, [$1_\alpha$, $2_\beta$, $3_\alpha$, $5_\alpha$]

EXAMPLE 3

DNA Synthesis in Swiss 3T3 Cells

Swiss mouse 3T3 cells were maintained in Dulbecco's modified Eagle's medium (DMEM) low glucose and supplemented with 10% fetal bovine serum (FBS), 2 mM 1-glutamine and 1% antibiotic-antimycotic 100X. The cultures were incubated in 5% $CO_2$ in air at 37° C. Confluent cultures were trypsinized and plated in quadruplicate cultures for experiments. Cells were plated at $1 \times 10^5$ cells per 35 mm well in DMEM containing 10% FBS in 6-well cluster plates and allowed to become confluent in 3 days. The cells were then made quiescent by washing them with Hank's balanced salt solution (HBSS) and incubating them for 24 hours in DMEM with 0.5% FBS. The cultures were then refed fresh DMEM containing 0.5% FBS and various concentrations of the compounds of interest. All compounds were dissolved in absolute ethanol, diluted with sterile filtered normal saline and added to the medium so that the final ethanol control cultures were incubated in medium containing 0.01% or less. The vehicle control cultures were incubated in medium containing 0.01% ethanol in saline. Cultures were incubated for 22 hours before pulse-labeling with ([$^3H$]-TdR), Pulse-labeling of the cultures consisted of collecting the conditioned, drug-treated or control containing media, then adding 1μ Ci/ml[$^3H$]-TdR and incubating the cultures in the [$^3H$]-TdR containing medium for 5 hours. The cells were then washed with phosphate buffered saline and fixed with 6% trichloroacetic acid (TCA). The cells were scraped from the culture wells and transferred to tubes. Each well was rinsed with 6% TCA and the rinse was added to the appropriate tubes. Each well was rinsed with 6% TCA and the rinse was added to the appropriate tubes. After centrifugation at 2800 RPM for 20 minutes at room temperature, an aliquot of the supernatant containing unincorporated [$^3$H]-TdR(S1) was transferred to scintillation tubes. Radioactivity was measured by liquid-scintillation counting using Beckman HP cocktail. The remainder S1 supernalant was decanted and 3% perchloric acid (PCA) was added to the cell pellet. The DNA was denatured by placing the tubes in heating blocks at 95° C. for 20 minutes, followed by placing the tubes in an ice bath for 15 minutes. After centrifugation as before, an aliquot of the supernatant containing [$^3$H]-TdR incorporated into DNA (S2) was assayed for radioactivity by scintillation counting.

An aliquot of the remaining S2 supernatant was assayed for quantity of DNA by the diphenylamine method. DNA standards, prepared from salmon testes DNA, and the samples were mixed with the diphenylamine reagent and incubated in a water bath with shaking at 30° C. for 6-24 hours. The diphenylamine reagent was prepared with 1.5% diphenylamine in glacial acetic acid and per 100 ml of the solution, by adding 1.5 ml of concentrated sulfuric acid and 0.5 ml of 1.6% acetaldehyde. Absorbance of the DNA standards and samples were measured in a Beckman Biomek spectrophotometer at 600 nM wavelength.

The data was expressed as CPM([$^3$H]-TdR incorporated into DNA) per ug DNA and the mean of the quadruplicate samples was obtained for each experiment. The results were presented as per cent of the vehicle control.

Table 2 shows that although PGF$_{2\alpha}$ and 17-phenyl PGF$_{2\alpha}$ potently increased DNA synthesis, replacement of the —COOH group by —OH resulted in a complete loss of activity. These results imply that the potential for fibrosis associated with prostanoids may be avoided by the nonacidic derivatives of this invention.

TABLE 2

| Inhibition of DNA Synthesis (E.C.$_{50}$ Values are 50% of maximal DNA synthesis response) | |
|---|---|
| PARENT COMPOUND (1-DERIVATIVE) | E.C.$_{50}$ [nM] |
| PGF$_{2\alpha}$ | 45 |
| A(OH) | >10,000 |

TABLE 2-continued

| Inhibition of DNA Synthesis (E.C.$_{50}$ Values are 50% of maximal DNA synthesis response) | |
|---|---|
| PARENT COMPOUND (1-DERIVATIVE) | E.C.$_{50}$ [nM] |
| 17-phenyl PGF$_{2\alpha}$ | 50 |
| B(OH) | >10,000 |

EXAMPLE 4

Vasorelaxation

The external rabbit jugular vein was used for vasorelaxation studies. A 3 mM ring was suspended in a 5 ml organ bath containing Krebs buffer and 1 μM indomethacin. The ring was pre-contracted with 10$^{-5}$M histamine to enable evaluation of vasorelaxation.

Results of these studies are given in Table 3. Potent vasodilator properties were apparent, the isopropylamide substituent unexpectedly provided a vasodilator with very high activity.

TABLE 3

| Vasorelaxation Reponses (E.C.$_{25}$ is the dose [M] to cause a 25% relaxation) | |
|---|---|
| COMPOUND (1-DERIVATIVE) | E.C.$_{25}$ [nM] |
| 17-phenyl PGF$_{2\alpha}$ | 57 |
| A(OH) | 40 |
| A(CONH$_2$) | 287 |
| A(CON(CH$_3$)$_2$) | 73 |
| A(CONH(isopropyl)) | 7.9 |

EXAMPLE 5

Smooth Muscle Stimulation

The ability of the nonacidic derivatives of this invention to contract a variety of smooth muscle preparations were determined. Isolated smooth muscle responses were evaluated in the conventional way, using an organ bath and a force displacement transducer. The preparations are the cat iris, ileum (guinea-pig and chick), rat colon, and rat aorta. Table 4 summarizes the results.

It can be seen that replacement of the carboxylic acid moiety results in compounds with minimal or absent contractile activity on the arterial smooth muscle (aorta) or ileum preparations. In contrast, surprisingly potent activity is retained for the cat iris and the rat colon.

TABLE 4

Comparison of Smooth Muscle Stimulant Properties
E.C.$_{50}$ values represent the concentration [M] required to produce 50% of the maximal PGF$_{2\alpha}$ effect.

| Compound (1-DERIVATIVE) | Cat Iris | Guinea Pig Ileum | Chick Ileum | Rat Colon | Rat Aorta |
|---|---|---|---|---|---|
| PGF$_{2\alpha}$ | 20 | 1900 | 1600 | 13 | 2,000 |
| A(CONH$_2$) | 21 | >10,000 | >10,000 | — | >10,000 |
| A(CON(CH$_3$)$_2$) | 450 | — | — | — | — |
| A(OH) | 60 | >10,000 | >10,000 | 81 | 4400 |
| A(OCH$_3$) | 60 | — | — | — | — |
| A(F) | 1500 | — | — | — | — |
| A(NO$_2$) | 1400 | — | — | — | — |
| A(NH$_2$) | — | >10,000 | — | — | >10,000 |
| A(I) | 700 | — | — | — | — |
| A(CN) | 420 | — | — | — | — |
| A(N$_3$) | 1000 | — | — | — | — |
| A(CH$_3$) | 230 | — | — | — | — |
| 17-phenyl PGF$_{2\alpha}$ | 11 | — | — | — | — |
| B(OH) | 62 | >10,000 | >10,000 | — | >10,000 |
| B(CONH$_2$) | 121 | >10,000 | >10,000 | — | >10,000 |
| B(CONH CH$_3$) | 56 | >10,000 | >10,000 | — | >10,000 |

TABLE 4-continued

Comparison of Smooth Muscle Stimulant Properties
$E.C._{50}$ values represent the concentration [M]
required to produce 50% of the maximal $PGF_{2\alpha}$ effect.

| Compound (1-DERIVATIVE) | Cat Iris | Guinea Pig Ileum | Chick Ileum | Rat Colon | Rat Aorta |
|---|---|---|---|---|---|
| $B(CON(CH_3)_2)$ | 670 | — | — | — | >10,000 |
| $B(CONH\ C_2H_5)$ | 34 | >10,000 | — | — | — |
| B(CONH isopropyl) | 175 | >10,000 | >10,000 | — | >10,000 |
| $B(NH_2)$ | 33 | — | — | — | — |
| 16-m-chlorophenoxy $PGF_{2\alpha}$ | 0.7 | >10,000 | 525 | — | 8060 |
| C(OH) | 4.2 | >10,000 | >10,000 | — | — |
| $C(CONH_2)$ | 30 | >10,000 | >10,000 | — | >10,000 |
| 13,14 dihydro 17-phenyl $PGF_{2\alpha}$ | 66 | >10,000 | 525 | — | — |
| D(OH) | 690 | >10,000 | >10,000 | — | — |

C is cyclopentane heptenoic acid, 5-cis-2-(3-α-hydroxy-4m-chlorophenoxy-1-trans-butenyl)-3,5-dihydroxy, [1α, 2α, 4α, 5β]

D is cyclopentane heptenoic acid, 5-cis-2-(3-α-hydroxy-5-phenylpentyl)-3,5-dihydroxy, [1α, 2α, 4α, 5β]

EXAMPLE 6

Intraocular Pressure

Intraocular pressure was measured by pneumatonometry in male and female Beagle dogs (10-15 kg). Studies were performed in conscious animals trained to accept pneumatonometry. Drugs were administered topically to one eye in a 25 μl volume drop, the contralateral eye received vehicle as a control. Statistical analysis was by Student's paired t test.

Replacement of the —COOH by a diverse variety of substituents resulted in potent ocular hypotensive agents, despite the inability of these agents to bind to prostanoid receptors or elicit a $Ca^{2+}$ second message as shown above. The intraocular pressure results are summarized in Table 5.

TABLE 5

Effect of Nonacid Derivatives on Intraocular Pressure

| COMPOUND (1-DERIVATIVE) | DOSE | IOP (mm Hg) at Predetermined Times (HR) After Dosing | | | |
|---|---|---|---|---|---|
| | | 2 | 4 | 6 | 24 |
| 17-phenyl $PGF_{2\alpha}$ | 0.01% | +1.6 | −2.7** | −3.0** | — |
| 17-phenyl $PGF_{2\alpha}$ | 0.1% | −2.2 | −4.8** | −5.9** | — |
| B(OH) | 0.01% | −.07 | −1.7 | −2.2 | — |
| B(OH) | 0.1% | −2.4 | −5.1 | −4.7** | — |
| $B(NH_2)$ | 0.1% | −0.9 | −1.0 | −2.3** | — |
| $B(CONH_2)$ | 0.1% | −2.7* | −4.1* | −5.7** | — |
| $B(CON(CH_3)_2$ | 0.1% | −2.8** | −4.4** | −4.9** | — |
| B(isopropylamide) | 0.1% | −2.0 | −5.1** | −5.6** | −3.7** |
| B(-methylamide) | 0.1% | −0.3 | −3.3** | −2.8* | 3.4** |
| B(ethylamide) | 0.1% | −0.3 | −2.8** | −4.9** | −2.8** |
| 16-m-chlorophenoxy $PGF_{2\alpha}$ | 0.1% | −1.5 | −3.4** | −1.6 | — |
| C(OH) | 0.01% | | | | |
| C(OH) | 0.1% | −3.1** | −3.2** | −4.7** | |
| $C(CONH_2)$ | 0.01% | | | | |
| $C(CONH_2)$ | 0.1% | −1.5 | −17** | −2.7* | |

*p < 0.05
**p < 0.01
n = 6

EXAMPLE 7

Inhibition of Neuronally Mediated Contraction of the Vas Deferens

Field stimulation of the isolated guinea-pig vas deferens results in contraction of the tissue. This provides a useful preparation for evaluating the effect of drugs on sympathetic neuronal transmission. 17-phenyl $PGF_{2\alpha}$ produced inhibition of this response whereas replacement of the —COOH moiety in this series of compounds resulted in either reduction or abolition of this activity (See Table 6 below).

TABLE 6

Inhibition of Contraction of the
Field-Stimulated Guinea Pig Vas Deferans
$E.C._{50}$ values represent the concentration [nM]
required to produce 50% of the maximal $PGE_2$ effect.

| COMPOUND (1-DERIVATIVE) | $E.C._{50}$ [nM] |
|---|---|
| 17-phenyl $PGF_{2\alpha}$ | 282 |
| $B(CONH_2)$ | >10,000 |
| B(OH) | — |
| $B(NH_2)$ | >10,000 |
| $B(CONH\ CH_3)$ | 2,188 |
| $B(CON(CH_3)_2)$ | >10,000 |

EXAMPLE 8

Cyclopentane methylheptenoate-5-cis-2 (3-αhydroxy-4-m-chlorophenoxy-1-trans-butenyl) -3,5 dihydroxy, [1α, 2β, 3α, 5α]

To a stirred solution of cyclopentane heptenoic acid, 5-cis-2-(3-αhydroxy-4-m-chlorophenoxy-1-trans-butenyl)-3,5-dihydroxy, [1α, 2β, 3α, 5α] (24 mg. 0.0565 mmol) in acetone (0.6 ml) at room temperature was added 1,8 diazabicyclo [5.4.0.] undec-7-ene (DBU) (40, ul, 0.27 mmol) and methyl iodide (20 ul, 0.32 mmol). The reaction turned yellow with the DBU addition. The reaction was maintained at room temperature for 6.5 hours, then was diluted with ethyl acetate (30 ml) and filtered through a plug of celite with the aid of ethyl acetate. After concentration in vacuo, the residue was flushed with ethylacetate (EtOAc) through a 20 mm×160 mm column of silica to give the desired methyl ester.

EXAMPLE 9

Cyclopentane heptenamide-5-cis-2-(3-αhydroxy-4-m-chlorophenoxy-1-trans-butenyl) -3,5 dihydroxy, [1α, 2β, 3α, 5α]

A mixture of the methyl ester of Example 8 (9.2 mg, 0.0222 mmol) and $NH_4Cl$ (10 mg, 0.187 mmol) in $NH_3$ was heated at 80° C. for 12 hours. After cooling to room temperature, the solvents were evaporated and the residue was subjected to column chromatography to provide the named amide as 7.2 mg of a clear, colorless liquid.

EXAMPLE 10

Cyclopentane methyl heptenoate-5-cis-2 (3-αhydroxy-5-phenyl-1-trans-pentenyl) -3,5dihydroxy, [1α, 2β, 3α, 5α]

To a stirred solution of cyclopentane heptenoic acid, 5-cis-2-(3-αhydroxy-5-phenyl-1-trans-pentenyl)-3,5 dihydroxy, [1α, 2β, 3α, 5α] (24 mg. 0.0565 mmol) in acetone (0.6 ml) at room temperature was added DBU (40, ul, 0.27 mmol) and methyl iodide (20 ul, 0.32 mmol). The reaction turned yellow with the DBU addition. The reaction was maintained at room temperature for 6.5 hours, then was diluted with ethyl acetate (30 ml) and filtered through a plug of celite with the aid of ethyl acetate. After concentration in vacuo, the residue was flushed with ethylacetate (EtOAc) through a 20 mm×160 mm column of silica to give the desired methyl ester.

EXAMPLE 11

Cyclopentane heptenamide-5-cis-2-(3-αhydroxy-5-phenyl-1-trans-pentenyl)-3, 5 dihydroxy, [1α, 2β, 3α, 5α]

A solution of the methyl ester of Example 10 and $NH_4Cl$ in $NH_3$ was heated at 80° C. for 36 hours in a sealed tube. After cooling the reaction vessel to −78° C., the plug was removed and the ammonia was allowed to evaporate while warming to room temperature. The residue was taken up in EtOAc (30 ml) and filtered through a plug of celite. Concentration in vacuo gave a clear, yellow oil that was purified by flash chromatography, using EtOAc, through a 160 mm×1 mm column of silica to give the desired amide.

EXAMPLE 12

Cyclopentane N, N-dimethylheptenamide-5-cis-2-(3-αhydroxy-5-phenyl-1-trans-pentenyl)-3, 5 dihydroxy, [1α, 2β, 3α, 5α]

A solution of the methyl ester of Example 10 (29.1 mg, 0.0723 mmol) and methanol (MeOH) (2 ml) in dimethylamine (8 ml) was heated at 80°–85° C. for 36 hours. After cooling to room temperature the sealed tube was opened and the excess amine was allowed to evaporate. Concentration of the residue in vacuo followed by flash chromatography with 10% EtOAc/MeOH through a 20 mm×120 mm column of silica to yield the named amide as 9.2 mg of a clear, slightly yellow oil and 14.8 mg of the recovered ester. Similarly the N-isopropyl, N-methyl and N-ethyl derivative can be prepared by substituting isopropylamine, methylamine and ethylamine, respectively for dimethylamine.

EXAMPLE 13

Cyclopentane hepteneamine-5-cis-2-(3-αhydroxy-5-phenyl-1-trans-pentenyl)-3, 5 dihydroxy, [1α, 2β, 3α, 5α]

To a solution of the amide of Example 11 in tetrahydrofuran (THF) at 0° C. was added dropwise a stock solution of lithium aluminumhydride (LiAlH) in THF. The reaction turned turbid white during this addition. After 2 hours, the reaction was removed from the cold bath and allowed to warm to room temperature over 15 minutes. Upon reaching room temperature, the reaction was quenched by cautious addition of 1N HCl (∼0.5 ml) then concentrated in vacuo to remove the THF. The residue was digested with ∼1 ml of 0.5 ml LiOH, then extracted into chloroform (5 ml). The chloroform layer was then concentrated in vacuo. Flash chromatography using an 8:1:1 EtOAc: MeOH: triethylamine ($Et_3N$) through a 10 mm×100 mm column of silica gel gave the desired amine as 10.7 mg of a clear oil. The oil was evaporated to constant weight on high vacuum overnight. Similarly, the 1-dimethylamino derivative can be prepared by substituting the 1-dimethylamido derivative of Example 12 for the amide of Example 11.

EXAMPLE 14

Cyclopentane heptenol-5-cis-2-(3-αhydroxy-5-phenyl-1-trans-pentenyl)-3,5 dihydroxy, [1α, 2β, 3α, 5α]

To a solution of cyclopentane heptenoic acid-5-cis-2-(3αhydroxy-5-phenyl-1-trans-pentenyl)-3, 5 dihydroxy, [1α, 2β, 3α, 5α] in ethyl ether ($Et_2O$) was added a $CH_2N_2$ solution until the mixture turned yellow. The mixture was then quenched with acetic acid until colorless. The solvents were removed under vacuum and residue pumped down on high vacuum for several hours. The resulting methyl ester was then taken up in $CH_2Cl_2$ and cooled to −78° C. in a dry ice/acetone bath. A dibutylaluminum hydride solution was then added hourly and the resulting reaction was allowed to warm to room temperature over 5 hours. The mixture was then quenched with MeOH. The resulting solution was transferred to a flask and diluted with ∼5 ml $CH_2Cl_2$. ∼5 ml of a saturated potassium sodium tartrate tetrahydrate solution was added and the resulting cloudy mixture was allowed to stir for 3 hours at which time the solution had cleared and the organic and water layers has separated. The mixture was transferred to a separatory funnel and separated. The organic layer was washed, consecutively, with ∼5 ml of $H_2O$ and ∼5 ml of brine, dried over $MgSO_4$ and concentrated to yield a yellow oil. Flash chromatography over $SiO_2$, with an eluant varying from 1% MeOH/$CH_2Cl_2$ to 5% MeOH/$CH_2Cl_2$ gave 32.2 mg of the desired product as a colorless oil.

EXAMPLE 15

Cyclopentane heptenol-5-cis-2-( 3-αhydroxy-4-m-chlorophenoxy-1-trans-butenyl)-3,5 dihydroxy, [1α, 2β, 3α, 5α]

To a solution of cyclopentane heptenoic acid-5-cis-2-(3-αhydroxy-5-phenyl-1-trans-pentenyl)-3, 5 dihydroxy, [1α, 2β, 3α, 5α] (24.0 mg, 0.0565 mml) in THF at 0° C. was added a stock solution of LiAlH (1.0 m, 0.11 ml, 0.11 mml). The resulting mixture was maintained at 0° C. for 2 hours, then was quenched by addition of 1N HCl (∼0.2 ml). The reaction was transferred into a separatory funnel with the aid of brine (5 ml) and $CHCl_3$ (10 ml). The layers were separated and the aqueous portion was further extracted with two 5 ml portions of $CHCl_3$. The combined organic layers were then concentrated and purified by passing through a column of silica using 5% MeOH in EtOAc as the eluant.

EXAMPLE 16

Cyclopentane heptenol-5-cis-2-(3-αtetrahydro-2H-pyran-2-yloxy-5-phenyl-1-trans-pentenyl)-3, 5 di-tetra hydro-2-H-pyran-2-yloxy, [1α, 2β, 3α, 5α]

A "protected" methylsulfonate ester of the named compound of Example 14 is prepared by preparing a derivative of said named compound, wherein said hydroxyl groups are protected by conversion into tetrahydropyranyl derivatives, by methods known in the art. For example, see U.S. Pat. No. 4,154,949 to Johnson et al, which issued 15 May 1979. Said derivatives are diluted in methylene chloride, cooled to 0° C., $Et_3N$ and $CH_3SO_2Cl$ are consecutively added and the organic layer is extracted and dried over $MgSO_4$. The solvent is evaporated to yield the methylsulfonate ester of the "protected" derivative. Similarly, the methylsulfonate ester of the "protected" derivative of Example 15 may be prepared by substitution of the named compound of Example 15 in the above preparation.

EXAMPLE 17

Cyclopentane heptenyliodide-5-cis-2-(3-αhydroxy-5-phenyl-1-trans-pentenyl)-3, 5 dihydroxy, [$1_\alpha$, $2_\beta$, $3_\alpha$, $5_\alpha$]

The "protected" compound of Example 16 is dissolved in acetone and then NaI and $CaCO_3$ are added. The mixture is stirred at room temperature over the weekend, filtered to remove $CaCO_3$ and then worked up with EtOAc, brine and $H_2O$. The aqueous layer is extracted with EtOAc, the extract combined with the organic layer and concentrated. The concentrate is dried over $MgSO_4$. The resulting product is recovered by evaporation of the remaining solvent. The resulting "protected" 1-iodide product is "deprotected" by dissolving in a mixture of MeOH and pyridinum-p-toluene sulfonate (PPTS) and heated, with stirring, to 50° C. The resulting solution is consecutively extracted with 10% citric acid, EtOAc, brine and $NaHCO_3$. The aqueous layer is extracted with EtOAc, the extract combined with the organic layer, concentrated and dried over $MgSO_4$. Upon evaporation the named compound is obtained. Similarly, the 4-m-chlorophenoxy-1-trans-butenyl derivative may be obtained by substitution of the methylsulfonate ester of the "protected" derivative of the compound of Example 15 in this preparation.

EXAMPLE 18

Cyclopentane hepteneazide-5-cis-2-(3-αhydroxy-5-phenyl-1-trans-pentenyl)-3, 5 dihydroxy, [$1_\alpha$, $2_\beta$, $3_\alpha$, $5_\alpha$]

The named compound is prepared by dissolving the "protected" compound of Example 16 in a solution of $NaN_3$ in dimethyl formamide (DMF) and stirring at room temperature for 20 hours. The resulting mixture is consecutively extracted with water, brine and EtOAc. The aqueous layer is extracted with EtOAc, the extract combined with the organic layer, concentrated and dried over $MgSO_4$. The solvent is evaporated and the residue is purified by chromatography using a solvent of 20% EtOAc in hexane. The resulting "protected" product is "deprotected" to yield the named compound by the procedure set forth in Example 17, above.

EXAMPLE 19

Cyclopentane methoxyheptene-5-cis-2-(3-αhydroxy-5-phenyl-1-trans-pentenyl)-3, 5 dihydroxy, [$1_\alpha$, $2_\beta$, $3_\alpha$, $5_\alpha$]

A solution of the "protected" compound of Example 16 in DMF is added dropwise to solution of NaH in DMF maintained under nitrogen at 0° C. with stirring. Stirring is continued and the solution is allowed to reach room temperature and stirring is continued for 15 minutes. The solution is then cooled to 0° C. and methyliodide is added and the solution is allowed to warm to room temperature. The resulting mixture is consecutively extracted with 10% citric acid, brine and EtOAc. The resulting aqueous layer is extracted with EtOAc, the extract is combined with the organic layer and the combination is dried over $MgSO_4$. Upon evaporation of the solvent a crude product including the tetrahydropyranyl derivative of the named compound is obtained. The crude product is purified by thin liquid chromatography (TLC) using a solvent comprising 30 to 40 percent EtOAc in hexane. The resulting hydropyranyl derivative is "deprotected" by use of the procedure of Example 17. The "deprotected" product is purified by TLC using a solvent comprising 1 to 5 percent acetic acid in EtOAc.

EXAMPLE 20

Cyclopentane heptenyl fluoride-5-cis-2-(3-αhydroxy-5-phenyl-1-trans-pentenyl)3, 5 dihydroxy, [$1_\alpha$, $2_\beta$, $3_\alpha$, $5_\alpha$]

The 0.098 mmoles of the compound of Example 16 (as derived from the Compound of Example 14) is dissolved into a 1.0 m. solution of tetrabutyl ammonium fluoride ($Bu_4NF$) in THF and stirred at room temperature overnight. (The total amount of $Bu_4NF$ is 0.196 mmoles.) TLC shows substantial sulfonate remained so an additional 2.0 m. (4 m. total) of $Bu_4NF$ is added. The mixture is stirred at room temperature for an additional 8 hours at which time it is then warmed up using $H_2O$, brine and EtOAc. The aqueous layer was extracted 3 times 10 ml. with EtOAc while the organic layer was concentrated, and dried using $MgSO_4$. The solvents were evaporated to yield 65 mgs. of the "protected" derivative of the named compound. The "protected" derivative of the named compound is purified using a 20% EtOAc/Hexane. The "protected" derivative of the named compound is "deprotected" by use of the method of Example 17 to yield the named compound.

EXAMPLE 21

Cyclopentane heptenyl nitrate-5-cis-2-(3-αhydroxy-5-phenyl-1-trans-pentenyl)-3, 5 dihydroxy, [$1_\alpha$, $2_\beta$, $3_\alpha$, $5_\alpha$]

The named compound is prepared by substituting $NaNO_2$ in the method of Example 20. Alternatively, the named compound is prepared by reacting the "protected" 1-iodide product of Example 17 with $NaNO_2$ in dimethylsulfoxide (DMSO) and "deprotecting" the resulting product as shown in Example 17.

EXAMPLE 22

Cyclopentane heptenecyanide-5-cis-2-(3-αhydroxy-5-phenyl-1-trans-pentenyl)-3, 5 dihydroxy, [$1_\alpha$, $2_\beta$, $3_\alpha$, $5_\alpha$]

The named compound is prepared by substituting NaCN in the method of Example 20.

EXAMPLE 23

Cyclopentane heptene-5-cis-2-(3-αhydroxy-5-phenyl-1-trans-pentenyl)-3, 5 dihydroxy, [$1_\alpha$, $2_\beta$, $3_\alpha$, $5_\alpha$]

0.293 mmoles of cyclopentafuran-2-one, 5-tetrahydropyranyloxy, 4-(3-tetrahydropyranyloxy- 1-octene) is dissolved in $CH_2Cl_2$, cooled to −78° C. and 1.0 Molar DiBAH in $CH_2Cl_2$ is added until 0.586 mmole of DiBAH is in solution. Stirring is continued for 2 hours and the reaction mixture is quenched with methanol.

The quenched mixture is washed into a separatory funnel with 10 ml of Ch2Cl2 and washed with water. Acetic acid is added until the layers separate. The organic layer is washed with brine. The combined water layers are washed twice with C2Cl2. The combined organic layers are dried over MgSO4 and concentrated to yield a lactol derivative. 0.331 mmols of the lactol derivative are added to a solution of 0.993 mmols, each, of (triphenyl) (n-pentyl) phosphonium bormide and KN(Si(CH3)3)2 in THF at −78° C. The resulting solution is allowed to warm to room temperature, overnight, and then separated with 20 ml of EtOAc and washed with dilute acetic acid, water and brine, consecutively. The organic layer is dried over Mg2SO4 and concentrated to yield a yellow oil which is purified by TLC with EtOAc/Hexane. The resulting "protected" derivative is "deprotected" by the method of Example 17 to yield cyclopentane heptene-5-cis-2-(3-αhydroxy-5-octenyl)-3, 5 dihydroxy, [1α, 2β, 3α, 5α]. The named compound is prepared by substituting the phenyl pentenyl derivative for the above named cyclopentafuran-2-one.

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

We claim:

1. A method of treating ocular hypertension which comprises applying to the eye an amount sufficient to treat ocular hypertension of a compound of formula III.

wherein hatched lines indicate α configuration and solid triangles indicate β configuration, and the dashed bonds represent a single or double bond which can be in the cis or trans configuration; X is hydroxyl; one of $R_1$ and $R_2$ is =O, —OH or a —O(CO)$R_6$ group, and the other one is —OH or —O(CO)$R_6$, or $R_1$ is =O and $R_2$ is H; wherein $R_6$ is a saturated or unsaturated acyclic hydrocarbon group having from 1 to about 20 carbon atoms, or —(CH2)m$R_7$ wherein m is 0–10, and $R_7$ is cycloalkyl radical, having from to three seven carbon atoms, or a hydrocarbyl aryl or heteroaryl, wherein the heteroatom is selected from the group consisting of nitrogen, oxygen, and sulfur atoms and $R_3$ is hydroxyl.

2. The method of claim 1 wherein said compound is a compound of formula IV

3. The method of claim 2 wherein said compound is a compound of formula V.

and the 9- and/or 11 esters, thereof.

4. The method of claim 3 wherein said compound is selected from the group consisting of cyclopentane heptenol-5-cis-2-(3-αhydroxy-5-phenyl-1-trans-pentenyl)-3, 5 dihydroxy [1α, 2β, 3α, 5α] and cyclopentane heptenol-5-cis-2-(3α hydroxy-5-phenylpentyl) 3,5 dihydroxy, [1α, 2β, 3α, 5α].

5. The composition of claim 4 wherein said compound is selected from the group consisting of cyclopentane heptenol-5-cis-2-(3-α hydroxy-5-phenyl-1-trans-pentenyl)-3, 5 dihydroxy [1α, 2β, 3α, 5α] and cyclopentane heptenol-5-cis-2-(3α hydroxy-5-phenylpentyl) 3,5 dihydroxy, [1α, 2β, 3α, 5α].

6. A pharmaceutical composition for treating ocular hypertension which comprises a therapeutically-effective amount of a compound of formula III.

wherein hatched lines indicate α configuration and solid lines indicate β configuration, and the dashed bonds represent a single or double bond which can be in the cis or trans configuration; X is hydroxyl; one of $R_1$ and $R_2$ is =O, —OH or a —O(CO)$R_6$ group, and the other one is —OH or —O(CO)$R_6$, or $R_1$ is =O and $R_2$ is H; wherein $R_6$ is a saturated or unsaturated acyclic hydrocarbon group having from 1 to about 20 carbon atoms, or —(CH2)m$R_7$ wherein m is 0–10, and $R_7$ is cycloalkyl radical, having from to three seven carbon atoms, or a hydrocarbyl aryl or heteroaryl, wherein the heteroatom is selected from the group consisting of nitrogen, oxygen, and sulfur atoms and $R_3$ is hydroxyl or a pharmaceutically-acceptable salt thereof in combination with an ophthalmically-acceptable vehicle.

7. The composition of claim 6 wherein said compound is a compound of formula IV.

8. The composition of claim 7 wherein said compound is a compound of formula V.

and the 9- and/11 esters, thereof.

* * * * *

UNITED STATES PATENT AND TRADEMARK OFFICE
CERTIFICATE OF CORRECTION

PATENT NO. : 5,352,708
DATED : 4 October 1994
INVENTOR(S) : Woodward et al

It is certified that error appears in the above-indentified patent and that said Letters Patent is hereby corrected as shown below:

In the abstract; line 4; delete "either" and insert in place thereof —ether—

Column 3, line 39; delete "heteratom" and insert in place thereof —heteroatom—

Column 19, line 2; delete "$Ch_2Cl_2$" and insert in place thereof —$CH_2Cl_2$—

Column 19, line 10; delete "bormide" and insert in place thereof —bromide—

Column 19, line 62; after the second occurrence of "is" insert —a—

Column 19, line 63; delete " to three " and insert in place thereof —three to—

Column 20, line 59; after the second occurrence of "is" insert —a—

Column 20, line 60; delete "to three" and insert in place thereof —three to—

Signed and Sealed this

Tenth Day of January, 1995

Attest:

BRUCE LEHMAN

*Attesting Officer*    *Commissioner of Patents and Trademarks*